United States Patent [19]

Brinkmann et al.

[11] Patent Number: 4,959,138
[45] Date of Patent: Sep. 25, 1990

[54] MEASURING PROBE FOR THE POTENTIOMETRIC DETERMINATION OF ION CONCENTRATIONS

[75] Inventors: Heinz-Jürgen Brinkmann, Frankfurt am Main, Fed. Rep. of Germany; Hans W. Bühler, Waedenswil, Switzerland; Albert Lohrum, Frankfurt am Main, Fed. Rep. of Germany

[73] Assignee: Ingold Messtechnik AG, Urdorf, Switzerland

[21] Appl. No.: 232,007

[22] Filed: Aug. 15, 1988

Related U.S. Application Data

[63] Continuation-in-part of Ser. No. 646,300, Aug. 31, 1984.

[30] Foreign Application Priority Data

Sep. 7, 1983 [CH] Switzerland ............ 4889/83

[51] Int. Cl.⁵ ............................................. G01N 27/30
[52] U.S. Cl. .................................... 204/414; 204/401; 204/416; 204/435
[58] Field of Search ............... 204/414, 416–419, 204/435, 401

[56] References Cited

U.S. PATENT DOCUMENTS

| | | |
|---|---|---|
| 2,278,248 | 3/1942 | Darrah ............................ 204/431 |
| 3,077,446 | 2/1963 | Van Den Berg ................. 204/435 |
| 3,337,441 | 8/1967 | Goldsmith ....................... 204/430 |
| 3,455,793 | 7/1969 | Watanabe et al. ............... 204/435 |
| 3,461,055 | 8/1969 | Staunton ......................... 204/435 |
| 3,705,089 | 12/1972 | Grubb .............................. 204/414 |
| 4,002,547 | 1/1977 | Neti et al. ........................ 204/435 |
| 4,092,232 | 5/1978 | Zetter .............................. 204/415 |
| 4,233,257 | 11/1980 | Maruyama et al. ............. 204/435 |
| 4,235,688 | 11/1980 | Sudrabin et al. ................. 204/435 |
| 4,282,079 | 8/1981 | Chang et al. .................... 204/435 |
| 4,390,406 | 6/1983 | Kato et al. ....................... 204/435 |

FOREIGN PATENT DOCUMENTS

| | | | |
|---|---|---|---|
| 3100302 | 12/1981 | Fed. Rep. of Germany | 204/435 |
| 3228647 | 2/1984 | Fed. Rep. of Germany | 204/435 |
| 2541462 | 8/1984 | France | 204/414 |
| 0039155 | 11/1979 | Japan | 204/435 |

Primary Examiner—T. Tung
Attorney, Agent, or Firm—Werner W. Kleeman

[57] ABSTRACT

A measuring probe in which the electrolyte is in the form of a highly viscous gel produced in situ from an ion-permeable polymer and a neutral salt suspension. Homogeneously suspended neutral salt particles in the gel cause the gel to have a turbid appearance which disappears progressively as the suspended neutral salt particles pass into solution, thus indicating at all times the state of aging of the electrolyte. The additional presence of silica gel renders the probe potential resistant to pressures in excess of 10 bars.

30 Claims, 2 Drawing Sheets

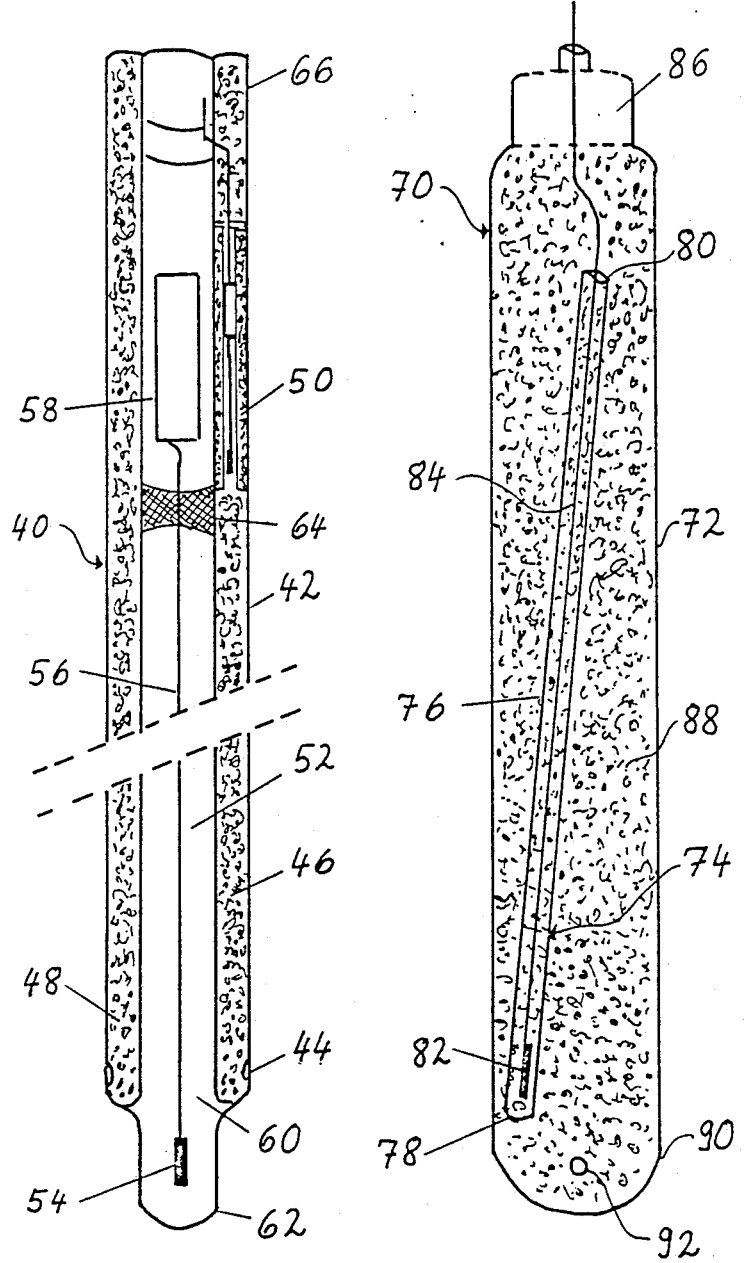

MEASURING PROBE FOR THE POTENTIOMETRIC DETERMINATION OF ION CONCENTRATIONS

CROSS REFERENCE TO RELATED APPLICATIONS

This application is a continuation-in-part of the commonly assigned, copending U.S. patent application Ser. No. 06/646,300, filed Aug. 31, 1984, entitled: "MEASURING PROBE FOR THE POTENTIOMETRIC DETERMINATION OF ION CONCENTRATIONS, PROCESS FOR ITS MANUFACTURE AND ITS APPLICATION" which is now abandoned and, in turn, related to the commonly assigned U.S. patent application Ser. No. 06/622,314, filed June 19, 1984, entitled "TEMPERATURE-INDEPENDENT SINGLE-ROD ELECTRODE ASSEMBLY FOR POTENTIOMETRIC MEASUREMENTS" and which is now abandoned.

BACKGROUND OF THE INVENTION

The present invention broadly relates to measuring probes and, more specifically, to a new and improved construction of a measuring probe for the potentiometric determination of ion concentrations, a process for its manufacture and its application.

Generally speaking, the measuring probe of the present invention is intended for the potentiometric determination of ion concentrations and comprises a reference element, an electrolyte and a housing formed of electrically insulating material provided with at least one hollow space for containing the reference element and the electrolyte and also having an aperture via which the electrolyte may be brought into contact with a sample solution located outside the housing. The measuring probe also comprises an ion-permeable polymer at least partially filling the hollow space. Pores of the ion-permeable polymer contain the electrolyte.

Numerous measuring probes of many different kinds for the potentiometric determination of ion concentrations and/or ion activities are known in the prior art. Generally, these comprise a diaphragm, which may be in the form of a porous rod of ceramic material, via which a reference and/or a bridge electrolyte contained within the probe and usually in liquid form may be brought into contact with the sample solution being measured. However, if measuring probes of this kind are used, in particular for monitoring and/or controlling microbiological processes, contamination of the diaphragm may lead to vitiation of the measuring results, producing serious errors of up to 60 mV. It is known that the majority of erroneous measuring results are due to this cause.

Other measuring probes are also known in the prior art containing an electrolyte in gel form. Since the electrolyte in electrodes of this kind is already in gel form when it is introduced into the probe housing according to the prior art, it is impossible to avoid hollow spaces or voids within the housing, so that such measuring probes can in general only withstand pressures of up to 10 bars.

Further, German Patent Publication No. 3,100,302, published Dec. 10, 1981, describes a measuring probe suitable for the analysis of micro-quantities of biological liquids in which an aperture in the housing leading to the interior of the probe is closed by a gel containing an aqueous solution of a neutral salt, the space within the housing being filled entirely or partially with this salt solution and/or the gel which contains such salt solution and has been formed in situ. The gel used for this purpose has a comparatively low viscosity and a comparatively high water-permeability, with the consequence that, on the one hand, the probe can only be used under constant and non-critical conditions (constant temperature, for example 37° C., and no pressure), so that it is not suitable for industrial applications such as process monitoring and/or process control, while, on the other hand, special arrangements are required to counter the impoverishment of the gel in neutral salt during long-term operation owing to its high water-permeability, for example by providing a feed tube via which fresh neutral salt solution can be added under pressure from a reservoir.

In an other electrode construction such as known, for example, from Japanese Patent No. 54-39 155, published Nov. 26, 1979, a solid electrolyte like, for instance, potassium chloride is mixed with a liquid curable resin and the mixture is cured in situ. The desired electrolytic conductivity is obtained by soaking the cured mixture with water from a saturated potassium chloride solution.

Furthermore, from the "HANDBOOK OF PLASTICS AND ELASTOMERS", Editor Ch. A. Harper, McGraw-Hill Book Company, 1975, pages 8-18 through 8-27, different types of fillers such as finely divided silica are known to modify viscosity, pot life, exothermicity, cure shrinkage, density, heat resistance, thermal conductivity, thermal coefficient of expansion, strength, machinability, hardness, wear resistance, electrical properties, chemical and solvent resistance, friction characteristics, thermal shock resistance, adhesion and color in epoxy and polyester resins.

A reference electrode such as known, for example, from U.S. Pat. No. 4,002,547, granted Jan. 11, 1977, contains a saturated potassium chloride solution in a container made of a hydrophobic polymer with incorporated salt particles and a metal oxide filler.

A further drawback of measuring probes of this kind is that, after long periods of use, aging phenomena may occur, resulting in potential drifts which can have an adverse effect on measuring accuracy. It is difficult to monitor the aging effects on measuring probes of this kind without carrying out numerous and complicated measurements.

Another problem with measuring probes of the aforesaid kind which has not yet been solved in the prior art consists in the fact that the reference potential is often unstable over long periods of use, and generally falls off considerably, particularly when the probe is used under pressures in excess of 10 bars or under fluctuating pressure conditions, in the presence of ultrasonic vibrations or for measuring heavily contaminated sample solutions.

SUMMARY OF THE INVENTION

Therefore, with the foregoing in mind, it is a primary object of the present invention to provide a new and improved construction of a measuring probe which does not exhibit the aforementioned drawbacks and shortcomings of the prior art constructions.

Another and more specific object of the present invention aims at providing a new and improved construction of a measuring probe of the previously mentioned type which does not require a diaphragm, so that a highly constant reference potential is ensured even with heavily contaminated sample solutions, under pressure and in the presence of ultrasonic vibrations, and which measuring probe will withstand pressures considerably in excess of 10 bars, and whose state of aging can be rapidly and simply ascertained.

Yet a further significant object of the present invention aims at providing a new and improved construction of a measuring probe of the character described which is relatively simple in construction and design, extremely economical to manufacture, highly reliable in operation, not readily subject to breakdown or malfunction and requires a minimum of maintenance and servicing.

Now in order to implement these and still further objects of the invention, which will become more readily apparent as the description proceeds, the measuring probe of the present invention is manifested by the features that it comprises an ion-permeable polymer formed in situ in the housing and filling the hollow space within the housing, the ion-permeable polymer being microporous, highly viscous, mechanically stable and containing a finely divided oxide rendering the ion-permeable polymer capable of withstanding pressures in excess of 10 bars; an electrolyte consisting of a suspension of homogeneously distributed particles of a neutral salt with ions of the same transport numbers in an aqueous solution of the neutral salt; and the polymer and the neutral salt suspension conjointly forming a gel having a turbid or cloudy appearance due to the presence of the neutral salt particles in suspension.

The process of manufacturing the measuring probe according to the present invention is manifested by the features that an aqueous solution of a neutral salt is prepared, finely-divided particles of the same neutral salt are added to the neutral salt solution, the suspension thus obtained is mixed with at least one of the monomers or prepolymers required for forming the ion-permeable polymer, a finely-divided oxide is also added to the monomer(s) or prepolymer(s), the liquid mixture thus obtained is subsequently introduced into the housing where it is then polymerised until it reaches a predetermined viscosity, and measures are undertaken to ensure that the neutral salt particles are homogeneously distributed throughout the gel resulting from polymerization.

The application of the measuring probe according to the present invention is manifested by the feature that it is intended to be employed in process control, process monitoring or in both.

It is one advantage of the measuring probe according to the invention that the measuring probe, due to the presence of the finely divided oxide, is highly pressure-resistant, so that it can withstand pressures of well over 10 bars, even up to the region of at least 70 bars, and that its electrode potential is virtually independent of pressure in the pressure range of over 10 to at least 70 bars.

Yet another advantage of the measuring probe according to the invention is that its state of aging is readily visible and can be continually monitored without the need for additional and complicated measurements. This possibility is due to the fact that the electrolyte is present in the form of a homogeneous suspension of particles of a neutral salt comprising ions of the same transport number in an aqueous solution of the same salt, so that the finely-divided particles of the neutral salt give rise to a turbid or cloudy appearance of the polymer in which they are held in suspension. As aging proceeds, this turbidity or cloudiness disappears as the finely-divided particles of the neutral salt pass into solution, until a final state is reached in which the solution appears almost clear.

Between a first zone in which there prevails the original state of finely-divided neutral salt particles in homogeneous suspension and a second zone in which the neutral salt particles have passed into solution, there exists a clearly visible phase boundary whose progressive movement may be readily observed. Both the state and rate of aging may be assessed from the position of the phase boundary and the speed of its migration.

Particularly favorable conditions with respect to the pore size, the viscosity of the polymer and its ability to absorb electrolytes in suspension form while ensuring a favorable diffusion rate are obtained with a polymer consisting of a homo-polymer or co-polymer of acrylamide or of methacrylamide with acrylic acid or methacrylic acid, a hydroxyalkylmethacrylate, vinyl alcohol or an epoxide or polyvinylpyrrolidone, preferably a copolymer of acrylamide with N,N'-methylenebisacrylamide. It is particularly advantageous for the pore size of the polymer to be of the same order of magnitude as the radius of a water molecule, in particular not more than $30 \times 10^{-10}$ m (=30 Angstroms). This polymer contains a finely divided oxide, such as $SiO_2$, $Al_2O_3$ or $TiO_2$, preferably silica gel. The proportion of silica gel in the ion-permeable polymer is in the range of 30% to 1000%, preferably 100% to 400%, and particularly 200% to 300% by weight of the anhydrous polymer. The particle size of the silica gel lies within the range of 0.01 to 0.5 mm, preferably 0.03 to 0.2 mm and particularly 0.05 to 0.15 mm.

An especially high viscosity and elasticity, of the gel formed by the polymer and the electrolyte is obtained by adding the aforementioned finely divided oxides, especially in the aforementioned quantities and particle sizes. Such finely divided oxides not only confer a significant increase in viscosity, but also a considerable improvement in mechanical stability. It is particularly significant that such gels impart high pressure resistance to the inventive measuring probe, i.e. the electrode potential does not vary or is subject only to insignificant variations when the measuring probe is exposed to pressures in excess of 10 bar, for example, up to at least 70 bar. These oxides further act as adsorption media for xeno-ions.

Compositions of the electrolyte in which the particle size of the silica gel lies within the aforementioned ranges and in which the neutral salt is potassium chloride, in which the electrolyte consists of a suspension of finely divided particles of potassium chloride in an aqueous or partially aqueous solution of potassium chloride, whereby the proportion of suspended potassium chloride particles in the ion-permeable polymer is in the range of 30% to 1500%, preferably 100% to 800% and particularly 200% to 400%, by weight of the anhydrous polymer, and in which the particle size of the potassium chloride lies within the range of 0.01 to 0.5 mm, preferably 0.03 to 0.2 mm and particularly 0.05 to 0.15 mm permit versatility in the field of application of the measuring probe according to the invention. Thus, it has been found that the electrode potential of the inventive measuring probe is only insignificantly affected by high pressures in excess of 10 bar, particularly up to at least 70 bar, and by fluctuating pressures such as produced, for example, by ultrasonic vibration, even in contact with highly contaminated solutions like, for instance, a paper mill effluent.

The addition of a water-vapor partial-pressure depressant, such as glycerine or ethylene glycol, whereby glycerine is particularly preferred, enables the measuring probe in accordance with the invention to be stored for long periods without the need for special precautions to be taken against drying-out.

A particularly advantageous and easily constructed embodiment of a measuring probe according to the invention is one in which the measuring probe is made either in the form of a reference electrode or in the form of a single-rod electrode assembly. In the form of a reference electrode, the measuring probe comprises a cartridge-type reference element containing an electrode and an internal reference electrolyte, the reference element being surrounded by the gel composed of the ion-permeable polymer containing the neutral salt suspension and the finely divided oxide. In the form of a single-rod electrode assembly, the measuring probe comprises a reference element in the form of an open-ended cartridge with the internal reference electrolyte in the form of a mixture with the same polymer as that constituting the gel. In the latter case, the reference electrolyte and/or the bridge electrolyte may be in the form of a gel as described in the foregoing text.

In the process for manufacturing the measuring probe, an aqueous solution of the neutral salt is prepared to which finely divided particles of the neutral salt are added and the suspension thus obtained is mixed with at least one of the monomers or prepolymers required for forming the polymer. A finely divided oxide is also added to the monomer(s) or prepolymer(s), after which the liquid mixture thus obtained is introduced into the housing, where it is then polymerized until it reaches a predetermined viscosity. Measures are undertaken to ensure that the neutral salt particles are homogeneously distributed throughout the gel resulting from polymerisation. This manufacturing process enables a measuring probe according to the invention to be produced simply, rapidly, and at low cost. This process also offers the advantage that the viscosity of the gel composed of the ion-permeable polymer, the neutral salt suspension and the finely divided oxide can be exactly matched to suit the required conditions, while at the same time avoiding the formation of undesirable empty spaces or voids liable to cause destruction of the measuring probe when subjected to external pressure. A further advantage is that it is possible, by judicious choice of the monomer and/or prepolymer required to form the final polymer, to control exactly the pore size of the aforementioned final polymer and hence its diffusion characteristics.

In a preferred embodiment of the invention, the neutral salt is potassium chloride, a suspension of which is prepared by the addition of solid potassium chloride particles to a 3 mol/l solution of potassium chloride. In another preferred embodiment a cross-linking agent, possibly accompanied by a cross-linking catalyst, is added to the monomer(s) or prepolymer(s). In yet another preferred embodiment the monomer is acrylamide and the cross-linking agent is N,N'-methylenebisacrylamide.

A measuring probe of the kind mentioned at the beginning of the present disclosure may be used for process monitoring and/or process control under conditions in which it is subjected to pressures in excess of 10 bars, in effect up to at least 70 bars. The possibility of continually checking the state of aging of the measuring probe by simple means ensures that a high degree of measuring accuracy is maintained even over long periods of use.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 4 shows a fragmentary longitudinal section of a measuring probe in the form of a single-rod electrode assembly; and FIG. 5 shows a schematic longitudinal section of a measuring probe having an elongated diffusion path.

DETAILED DESCRIPTION OF THE PREFERRED EMBODIMENTS

Figure 1:
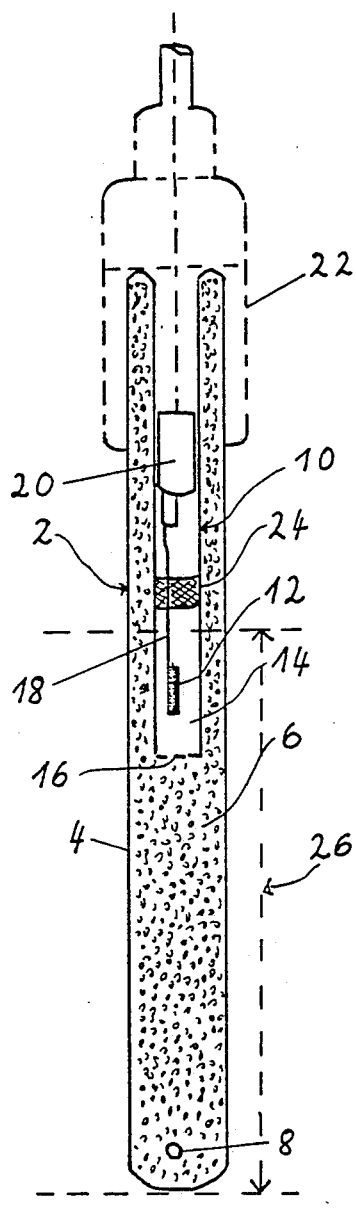
FIG. 1 shows a longitudinal section of a measuring probe in the form of a reference electrode.

Describing now the drawings, it is to be understood that to simplify the showing of the drawings only enough of the structure of the measuring probe is shown therein as is needed to enable one skilled in the art to readily understand the underlying principles and concepts of this invention. Turning now specifically to FIG. 1, the apparatus illustrated therein will be seen to comprise a measuring probe 2 in the form of a reference electrode, with a housing 4 formed of electrically insulating material, for example glass, or a synthetic material such as polyethylene. The housing 4 serves to contain a reference electrolyte 6 which is brought into contact with a sample solution not shown in the figure via at least one aperture 8 when the measuring probe 2 is immersed in the sample solution to be measured.

The reference electrolyte 6 is in the form of an ion-permeable microporous gel of high viscosity, for example 10,000 cP, containing a finely divided oxide, particularly silica gel, and is preferably composed of a copolymer of acrylamide with N,N'-methylenebisacrylamide, the porous spaces of which are filled with a suspension of finely divided particles of a neutral salt with ions of the same transport number in a solution of the same salt, whereby the neutral salt is preferably potassium chloride. Owing to the presence of finely divided neutral salt particles in suspension, the gelled reference electrolyte 6 has an evenly distributed cloudy or milky appearance.

The reference electrolyte 6 surrounds a reference element 10 in the form of a cartridge open at one end, and likewise contained within the housing 4. The reference element 10 contains an electrode 12 of known potential, for example an Ag/AgCl electrode comprising a chlorided silver wire immersed in a KCl solution serving as an internal reference electrolyte 14. To prevent the internal reference electrolyte 14 from flowing out via the open end 16 of the reference element 10, the internal electrolyte 14 is held within the pore spaces of an ion-permeable microporous polymer, preferably of the same composition as that containing the reference electrolyte 6. At the end of the reference element 10 and lying opposite the open end 16 there is located a socket contact 20, connected to the electrode 12 via a conductor 18, which may be of platinum wire, such that electrical connection may be made between the socket contact 20 and connecting elements situated either in the head 22 of the measuring probe or outside the housing 4. Further, a seal or barrier element 24, for example made of glass or of synthetic material, is placed inside the reference element 10 to prevent the socket contact 20 from coming into direct contact with the internal reference electrolyte 14.

A preferred embodiment of the process for manufacturing the measuring probe 2 consists in that the reference element 10 is introduced into the housing 4, after which the latter is evacuated and a mixture of the monomers and/or prepolymers required to form the final polymer, accompanied if necessary by polymerising and/or cross-linking catalysts, and the neutral salt suspension comprising the homogeneously distributed, finely divided neutral salt particles suspended in the solution of the same netural salt, is sucked into the housing 4, where the mixture is polymerised and/or cross-linked after admixture of the finely divided oxide.

A preferred embodiment of the process according to the invention makes use of a mixture of acrylamide and N,N'-methylenebisacrylamide, in which the proportion of N,N'-methylenebisacrylamide is from 1 percent to 5 percent by weight of the total mixture, to which one or more polymerizing catalysts are added. Preferred catalysts for chemical polymerisation are ammonium peroxodisulphate $((NH_4)_2S_2O_8)$ and tetramethylethylenediamine

$((CH_3)_2N(CH_2)_2N(CH_3)_2)$ advantageously added together, while preferred catalysts for photopolymerisation are riboflavine and tetramethylethylenediamine, likewise advantageously added together. The use of the aforesaid mixture results in a copolymer of acrylamide and N,N'-methylenebisacrylamide possessing a cross-linked structure and particularly favorable diffusion, stability and viscosity characteristics.

The gel further contains a finely divided oxide or mixture of oxides, such as $SiO_2$, $Al_2O_3$ and/or $TiO_2$. A particularly suitable additive for this purpose is silica gel, which significantly increases pressure resistance of the final measuring probe and renders the electrode potential substantially independent of pressure up to pressures of at least 70 bars. Furthermore, silica gel not only increases the viscosity and elasticity, but also causes a significant improvement in mechanical stability. A further function of the aforesaid oxides is to act as adsorption agents for xeno-ions infiltrating from the sample solution under measurement.

While the mixture of monomers and/or prepolymers, cross-linking catalyst and silica gel is yet in the liquid state, the neutral salt suspension, preferably a suspension of finely divided KCl particles in a 3 mol/l aqueous solution of potassium chloride, is added to it. The size range of the solid KCl particles is preferably 0.03 mm to 0.2 mm, and particularly 0.05 mm to 0.15 mm. The quantity of potassium chloride should be selected such that the KCl content of the final polymer is at least 30%, for example 30% to 1500%, preferably 100% to 800%, and particularly 200% to 400% by weight of the dry polymer.

This mixture, when polymerisation is completed, gives a high-viscosity microporous gel. The gel is characterized by very good mechanical stability and a negligibly low water permeability. The latter property prevents impoverishment of the gel in KCl even during long-term operation.

To prevent the gel from drying out even when stored for long periods without special protection, a water-vapor partial-pressure depressant may be added to the starting mixture from which the gel is formed. Suitable depressants for this purpose are glycerine, ethylene glycol or similar substances, whereby glycerine is preferred.

Since the gel is formed in situ inside the housing 4, on the one hand complete filling of the space inside the housing 4 can be achieved, while on the other hand it is possible to create a viscosity higher than that which could be obtained if the mixture forming the reference electrolyte 6 were to be subsequently filled into the housing. This high viscosity of the reference electrolyte 6 confers the advantage that no diaphragm is required to close off the aperture 8. At the same time, the complete filling of the space inside the housing 4 by the reference electrolyte 6 contributes to the aforenoted high pressure resistance of the inventive measuring probe 2 to pressures up to at least 70 bar.

The finely divided neutral salt particles suspended in the gelled electrolyte 6 cause the electrolyte to present a uniform cloudy or turbid appearance, which in the initial state extends over the whole length of the housing 4 filled with the reference electrolyte 6. This cloudiness or turbidity, whose intensity depends upon the concentration and/or size of the neutral salt particles in suspension, is clearly visible to the naked eye.

As aging proceeds, the finely divided neutral salt particles held in suspension in the gelled reference electrolyte 6, pass progressively into solution, thus gradually producing a solution which has a considerably lower degree of cloudiness or turbidity, the latter only being present due to the presence of the suspended silica gel. This process is indicated by a marked decrease in the cloudiness or turbidity, whereby the cloudiness or turbidity due to the suspended neutral salt particles completely disappears from that part of the gelled reference electrolyte 6 in which the particles have passed into solution, leaving only the very slight cloudiness or turbidity due to the silica gel. The sector 26 of the measuring probe 2 is particularly suitable for observing this phenomenon.

Figure 2:
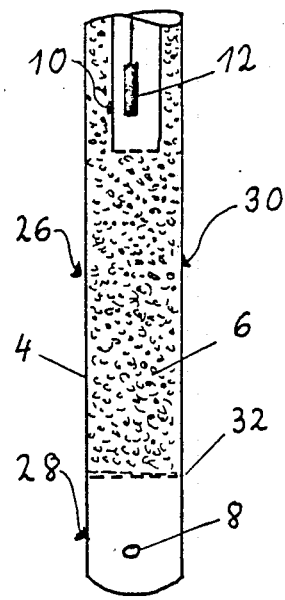
FIG. 2 shows a partial longitudinal section of a measuring probe according to FIG. 1 in an early state of aging.
Figure 3:
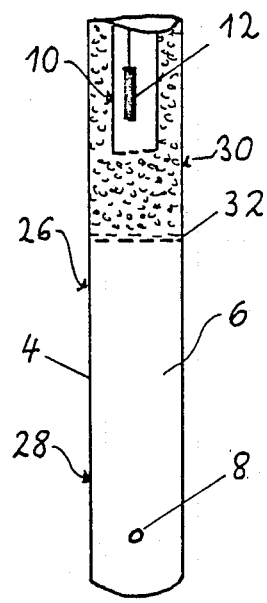
FIG. 3 shows a partial longitudinal section of a measuring probe according to FIG. 1 in a later state of aging.

FIGS. 2 and 3 illustrate the sector 26 of the measuring probe 2 shown in FIG. 1 at different stages of aging, whereby FIG. 2 shows an early stage of aging and FIG. 3 shows a more advanced stage of aging.

It will be seen from FIG. 2 that in a first zone 28 in the vicinity of the aperture 8 in the housing 4 the reference electrolyte 6 exhibits a degree of cloudiness or turbidity which is only very slight in comparison with that of its initial state. This zone is optically almost clear, thus indicating that the reference electrolyte 6 in the zone 28 is free from suspended neutral salt particles. Conversely, in a second zone 30 in the vicinity of the reference element 10 the reference electrolyte 6 possesses its initial cloudiness or turbidity due to the presence of suspended neutral salt particles. In between the first zone 28 and the second zone 30 there lies a clearly visible phase boundary 32 whose position can be easily verified by visual inspection. In the early stage of aging shown in FIG. 2 the first zone 28 is small in comparison with the second zone 30, so that the phase boundary 32 is located in the vicinity of the aperture 8.

FIG. 3 illustrates a more advanced stage of aging in which the phase boundary 32 has been considerably displaced towards the reference element 10, so that the first zone 28 free from suspended neutral salt particles is now large in comparison with the second zone 30 still containing suspended neutral salt particles.

Since the phase boundary 32 is clearly visible, its migration towards the reference element 10 can easily be monitored by visual inspection. Further, since the state of aging of the reference electrolyte 6 in the measuring probe 2 may be determined from the position of the phase boundary 32, and the potential shift associated therewith is known, it is possible for the user to take cognisance of this state of affairs as the phase boundary 32 approaches the reference element 10 and hence take the necessary steps to compensate for the potential shift without the need for undertaking a complicated series of test measurements. At any time it is also possible for the user to determine either by calculation and/or by measurements any time lag which may occur between the approach of the phase boundary 32 to the reference element 10 and the onset of the aforesaid potential shift.

FIG. 4 illustrates an embodiment of the invention in which the measuring probe 40 is in the form of a single-rod electrode assembly with a housing 42 made of an electrically insulating material such as glass or a synthetic material, for example polyethylene. The housing 42 has at least one aperture 44 via which the reference electrolyte 48 contained in the annular space 46 immediately inside the walls of the housing 42 may be brought into contact with the sample solution under measurement by immersion of the probe 40 into the sample solution.

The annular space 46 also contains a reference element 50 of similar construction to the reference element 10 of the embodiment of the invention illustrated in FIG. 1. The annular space 46 surrounds an inner space 52 containing a lead-out electrode 54, for example a silver wire electrode. The lead-out electrode 54 is connected to a contact element 58 by means of a conductor 56, for example a platinum wire, and is surrounded by an internal buffer solution 60. In order to ensure ion exchange between the internal buffer 60 and a sample solution upon immersion of the measuring probe into the sample solution, the lower part of the inner space 52 is provided with an ion-sensitive membrane 62, for example a glass membrane. Further, a seal or barrier element 64 is placed in the inner space 52 in the vicinity of the contact element 58 to prevent the internal buffer solution 60 from coming into direct contact with the contact element 58 or with any other contact elements such as may be located either within the head 66 of the measuring probe 40 or outside the housing 42 of this measuring probe.

The measuring probe 40 may be manufactured in a similar manner to the measuring probe 2 already described. The functioning of the measuring probe 40 closely resembles that of the measuring probe 2, particularly with respect to the monitoring of the state of aging.

FIG. 5 illustrates diagrammatically a measuring probe 70 with a considerably elongated diffusion path. The measuring probe 70 has a housing 72 made of an electrically insulating material such as glass or a synthetic material, for example, polyethylene. The housing 72 contains a reference electrode 74 in cartridge form, of similar construction to that of the measuring probe 2 and with a tubular housing 76 corresponding to the tubular housing 4 of the reference electrode in the measuring probe 2, but distinguished from the latter in that the lower end 78 of the tubular housing 76 is closed, i.e. possesses no aperture, whereas the upper end 80 of the tubular housing 76 is open. The reference electrode 74 contains an internal electrode 82, for example an Ag-/AgCl electrode, connected via a conductor 84, for example a platinum wire, to a contact element which may be located either inside the head 86 of the housing 72 or outside the housing.

The reference electrode 74 is completely surrounded by a gelled electrolyte 88 which entirely fills the housing 72. The composition of the electrolyte 88 is identical with that of the electrolyte in the reference electrode 74 and corresponds, for example, to that of the aforementioned reference electrolyte 6. An aperture 92 located at the lower end 90 of the housing 72 enables the electrolyte 88 to be brought into contact with a sample solution not shown in the figure when the measuring probe 70 is immersed in such sample solution to be measured.

It will be seen from FIG. 5 that the diffusion path, i.e. the distance over which the phase boundary must migrate from the aperture 92 in order to reach the internal reference electrode 82, is considerably longer than in the case with the measuring probe 2 illustrated in FIG. 1. This path runs from the aperture 92 right up to the upper end 80 of the tubular housing 76 and thence down to the internal reference electrode 82.

Now, as aging proceeds, the phase boundary between the only slightly clouded or turbid solution in which all the neutral salt particles are dissolved, and the suspension whose heavy cloudiness or turbidity is due to the presence of undissolved neutral salt particles, first migrates upwards from the aperture 92 up to the open upper end 80 of the tubular housing 76 and then downwards within the tubular housing 76 until it reaches the internal reference electrode 82. Only when the phase boundary has reached the internal reference electrode 82 will the potential of the internal reference electrode begin to drift. For this reason, the embodiment of the invention illustrated in FIG. 5 has a considerably longer working life than that illustrated in FIG. 1.

EXAMPLE

A first aqueous solution was made up from 40 g acrylamide, 2.75 g methylenebisacrylamide and 0.23 ml N,N,N',N'-tetramethylethylenediamine in 200 ml of 3 mol/l potassium chloride solution.

A second solution was made up with 0.14 g ammonium peroxodisulphate in 200 ml of 3 mol/l potassium chloride solution. Both solutions were stirred with a magnetic stirrer until complete homogeneity was obtained.

The first solution was degassed with a filter pump, after which the two solutions were mixed in a suitably large beaker. Immediately after mixing, 120 g solid potassium chloride with a particle size smaller than 0.1 mm and 120 g finely divided silica gel were added. The combined mixture was then carefully maxillated to obtain a homogeneous paste, into which 15 electrodes were then inserted and subjected to a low pressure in a vacuum dessicator for 3 minutes.

Air was then slowly admitted to the dessicator, whereupon the paste was sucked into the electrodes. The electrodes were left in the beaker until polymerisation was complete, after which they were ready for further processing. The pot-life of the polymer was approximately 20 minutes.

For comparison purposes, electrodes were produced in substantially the same manner but without the addition of silica gel to the polymer.

1-Pressure Resistance

The electrodes produced in the above described manner were immersed into (A) a physiological buffer solution on a phosphate basis and (B) an isotonic physiological buffer solution on a phosphate basis and containing a predetermined concentration of sodium chloride. The physiological buffer solutions were subjected to pressure cycles between atmospheric pressure and 70 bars and pH values were measured after each pressure change of 10 bars. The measuring temperature was 19° C. The measuring results are shown in the following table:

| Pressure | Measured pH values | |
|---|---|---|
| (bar) | Solution A | Solution B |
| atm. | 7.960 | 7.410 |
| 10.0 | 7.961 | 7.411 |
| 20.0 | 7.962 | 7.410 |
| 30.0 | 7.962 | 7.405 |
| 40.0 | 7.964 | 7.401 |
| 50.0 | 7.966 | 7.396 |
| 60.0 | 7.966 | 7.396 |
| 70.0 | 7.963 | 7.397 |
| 60.0 | 7.968 | 7.396 |
| 50.0 | 7.972 | 7.399 |
| 40.0 | 7.976 | 7.403 |
| 30.0 | 7.970 | 7.407 |
| 20.0 | 7.968 | 7.410 |
| 10.0 | 7.965 | 7.410 |
| atm. | 7.963 | 7.405 |

This table shows that the electrode potentials expressed as pH values are subject to only insignificant, i.e. negligibly small variations when the pressure is varied between atmospheric pressure and 70 bar.

Conventional pH measuring electrodes cannot be subjected to pressures in excess of 10 bar.

2-Resistance to pressure changes

By means of a pneumatic impulse circuit, the electrodes were alternatingly subjected to 15 minutes under a pressure of approximately 6 bars, followed by 15 minutes at normal atmospheric pressure. This test was carried out over 400 cycles at ambient temperature. The electrodes were immersed in a 1:1 mixture of drilling emulsion and redox buffer. A 10% potassium dichromate solution was then added to this mixture. These conditions, which are sometimes encountered in industrial practice, are highly detrimental to all reference systems.

The electrode potentials were measured before and after the test in various buffer solutions as well as in a 3 mol/1 KCl solution against a Hg/Hg$_2$Cl$_2$ reference electrode. The results are shown in the following table:

| Measuring Solution | Measured Electrode Potentials (mV) | | | |
|---|---|---|---|---|
| | SiO$_2$-Containing Electrode | | SiO$_2$-Free Electrode | |
| | Before Test | After Test | Before Test | After Test |
| Buffer, pH 4.01 | −42.5 | −41.7 | −33.9 | −21.5 |
| Buffer, pH 7.00 | −40.9 | −41.6 | −33.1 | −22.1 |
| Buffer, pH 9.21 | −42.0 | −43.3 | −33.2 | −24.1 |
| KCl | −41.5 | −40.4 | −33.1 | −16.9 |

It will be seen from the above table that the electrode containing silica gel in the ion-permeable polymer maintained an almost constant reference potential during the test, whereas the electrode potential of the electrode which did not contain silica gel in the ion-permeable polymer, fell off very considerably.

3-Resistance to ultrasonic vibration

The aforenoted electrodes were immersed in water and continuously subjected to ultrasonic vibration. The test was carried out over a period of two months at ambient temperature. Ordinary tap water was used as the medium. The electrode potentials were measured before and after the test in various buffer solutions as well as in a 3 mol/1 aqueous solution of KCl. The results are shown in the following table:

| Measuring Solution | Measured Electrode Potentials (mV) | | | |
|---|---|---|---|---|
| | SiO$_2$-Containing Electrode | | SiO$_2$-Free Electrode | |
| | Before Test | After Test | Before Test | After Test |
| Buffer, pH 4.01 | −41.9 | −41.0 | −34.8 | −20.9 |
| Buffer, pH 7.00 | −41.1 | −40.3 | −34.2 | −20.0 |
| Buffer, pH 9.21 | −42.5 | −41.2 | −33.9 | −18.5 |
| KCl | −41.1 | −40.7 | −34.1 | −19.5 |

It will again be seen that the electrode potential of the electrode containing the SiO$_2$-free ion-permeable polymer fell off considerably during the two months' test period under the influence of ultrasonic vibration, while that of the electrode according to the invention remained almost constant.

4-Resistance to heavily contaminated solutions

In a further test, effluent water from a paper mill with a low sulphide concentration (diluted 1:1 with water) was used as a medium. The electrodes were immersed in the medium and subjected continuously to ultrasonic vibration. The test period was again two months at normal ambient temperature.

| Measuring Solution | Measured Electrode Potentials (mV) | | | |
|---|---|---|---|---|
| | SiO$_2$-Containing Electrode | | SiO$_2$-Free Electrode | |
| | Before Test | After Test | Before Test | After Test |
| Buffer, pH 4.01 | −41.7 | −40.8 | −32.9 | −39.3 |
| Buffer, pH 7.00 | −41.1 | −40.5 | −32.2 | −37.4 |
| Buffer, pH 9.21 | −42.0 | −41.0 | −31.5 | −44.0 |
| KCl | −41.0 | −41.9 | −31.5 | −10.4 |

Here it will be seen that under these test conditions the electrode potential of the electrode containing the SiO$_2$-free ion-permeable polymer underwent considerable vibrations, sometimes increasing and sometimes decreasing. Such behavior is a typical symptom of a contaminated transfer zone between the reference electrolyte and the sample solution. With the electrode according to the invention, on the other hand, the electrode potential again remained almost constant and did not change due to the test.

While there are shown and described present preferred embodiments of the invention, it is to be distinctly understood, that the invention is not limited thereto, but may be otherwise variously embodied and practiced within the scope of the following claims. Accordingly,

What we claim is:

1. A measuring probe for the potentiometric determination of ion concentrations, comprising:
    a reference element containing an electrode immersed in an electrolyte and assuming a predetermined electrode potential;
    an electrolyte providing electrolytic conductive connection between said reference element and a sample solution to be investigated by means of the measuring probe;
    a housing of electrically insulating material;
    said housing being provided with at least one hollow space for containing said reference element and said electrolyte;
    the housing having at least one aperture via which said electrolyte may be brought into contact with said sample solution located outside the housing;
    said electrolyte comprising an ion-permeable microporous polymer gel formed in situ in said housing and filling said at least one hollow space;
    said ion-permeable microporous polymer gel comprising a polymer polymerized in situ in said housing in a suspension of silica gel in a saturated aqueous solution of a neutral salt containing suspended neutral salt particles;
    said silica gel incorporated in said ion-permeable microporous polymer gel rendering the measuring probe pressure resistant to pressures in excess of 10 bars;
    said predetermined electrode potential of said electrode being negligibly variable with pressure and pressure variations in the range of environmental pressure in excess of 10 bars due to the presence of said silica gel;
    said silica gel adsorbing xeno-ions and thereby rendering said predetermined electrode potential substantially independent of the presence of such xeno-ions in said electrolyte as the result of diffusion from sample solutions investigated using the measuring probe;
    the neutral salt forming said saturated aqueous solution containing ions having predetermined transport numbers; and
    said neutral salt particles suspended in said saturated aqueous solution being substantially homogeneously distributed throughout said ion-permeable microporous polymer gel and containing ions having transport numbers which are substantially the same as said predetermined transport numbers of said neutral salt dissolved in said saturated aqueous solution.

2. The measuring probe as defined in claim 1, wherein:
    said ion-permeable micorporous polymer gel assume a turbid appearance in the presence of said homogeneously distributed particles;
    said ion-permeable microporous polymer gel being subject to aging during continued use of the measuring probe due to the depletion of said neutral salt particles from said ion-permeable microporous polymer gel; and
    said ion-permeable microporous polymer gel indicating the state of aging of the measuring probe by formation of a distinct phase boundary between a substantially clear first zone which is depleted of said neutral salt particles, and a turbid second zone which still contains said neutral salt particles.

3. The measuring probe as defined in claim 1, wherein:
    said polymer is a homo-polymer of acrylamide or methacrylamide with acrylic acid or methacrylic acid, a hydroxyalkylmethacrylate, vinyl alcohol or polyvinylpyrrolidone.

4. The measuring probe as defined in claim 1, wherein:
    said polymer comprises a copolymer of acrylamide with N,N'-methylenebisacrylamide.

5. The measuring probe as defined in claim 1, wherein:
    the pore size of said ion-permeable microporous polymer gel is of the same order of magnitude as the radius of a water molecule.

6. The measuring probe as defined in claim 5, wherein said pore size is at most $30 \times 10^{-10}$ m.

7. The measuring probe as defined in claim 1, wherein:
    the proportion of said silica gel in said ion-permeable microporous polymer gel is in the range of 30% to 1000% by weight of the anhydrous polymer.

8. The measuring probe as defined in claim 7, wherein:
    the proportion of said silica gel in said ion-permeable microporous polymer gel is in the range of 100% to 400% by weight of the anhydrous polymer.

9. The measuring probe as defined in claim 8, wherein:
    the proportion of said silica gel in said ion-permeable microporous polymer gel is in the range of 200% to 300% by weight of the anhydrous polymer.

10. The measuring probe as defined in claim 1, wherein:
    said silica gel has a particle size in the range of 0.01 mm to 0.5 mm.

11. The measuring probe as defined in claim 10, wherein:
    the particle size of said silica gel lies within the range of 0.03 to 0.2 mm.

12. The measuring probe as defined in claim 11, wherein:
    the particle size of said silica gel lies within the range of 0.05 to 0.15 mm.

13. The measuring probe as defined in claim 1, wherein:
    said neutral salt dissolved in said saturated aqueous solution, comprises potassium chloride.

14. The measuring probe as defined in claim 1, wherein:
    said substantially homogeneously distributed neutral salt particles comprise finely divided particles of potassium chloride; and
    said finely divided particles of potassium chloride being present in said ion-permeable microporous polymer gel in a proportion in the range of at least 30% to 1500% by weight of the anhydrous polymer.

15. The measuring probe as defined in claim 14, wherein:
    said proportion of said finely divided particles of potassium chloride in said ion-permeable microporous polymer gel is
    in the range of 100% to 800% by weight of the anhydrous polymer.

16. The measuring probe as defined in claim 15, wherein:

said proportion of said finely divided particles of potassium chloride in said ion-permeable microporous polymer gel is in the range of 200% to 400% by weight of the anhydrous polymer.

17. The measuring probe as defined in claim 14, wherein:
said finely divided particles of potassium chloride have a particle size in the range of 0.01 to 0.5 mm.

18. The measuring probe as defined in claim 17, wherein:
said particle size of said finely divided particles of potassium chloride lies within a range of 0.03 to 0.2 mm.

19. The measuring probe as defined in claim 18, wherein:
said particle size of said finely divided particles of potassium chloride lies within a range of 0.05 to 0.15 mm.

20. The measuring probe as defined in claim 1, wherein:
said measuring probe contains a water-vapor partial pressure depressant in order to thereby prevent drying-out of said ion-permeable microporous polymer gel.

21. The measuring probe as defined in claim 20, wherein:
said water-vapor depressant comprises glycerine.

22. The measuring probe as defined in claim 20, wherein:
said water-vapor depressant comprises ethylene glycol.

23. The measuring probe as defined in claim 1, wherein:
said reference element is in the form of a cartridge;
an internal reference electrolyte of said reference element;
said electrode being immersed into said internal reference electrolyte; and
said reference element being accommodated in said ion-permeable microporous polymer gel.

24. The measuring probe as defined in claim 23, wherein:
said reference element in the form of said cartridge comprises a cartridge with an open end and
an internal reference electrolyte constituted by said ion-permeable microporous polymer gel containing said aqueous neutral salt and silica gel in suspension.

25. The measuring probe as defined in claim 1, wherein:
said measuring probe constitutes a reference electrode.

26. The measuring probe as defined in claim 1, wherein:
said measuring probe is in the form of a single-rod electrode assembly.

27. The measuring probe as defined in claim 1, wherein:
said measuring probe constitutes a process monitoring measuring probe.

28. The measuring probe as defined in claim 1, wherein:
said measuring probe constitutes a process control measuring probe.

29. The measuring probe as defined in claim 1, wherein:
said measuring probe constitutes a process monitoring and process control measuring probe.

30. A measuring probe for the potentiometric determination of ion concentrations, comprising:
a reference element containing an electrode immersed in an electrolyte and assuming a predetermined electrode potential;
an electrolyte providing electrolytic conductive connection between said reference element and a sample solution to be investigated by means of the measuring probe;
a housing of electrically insulating material;
said housing being provided with at least one hollow space for containing said reference element and said electrolyte;
the housing having at least one aperture via which said electrolyte may be brought into contact with said sample solution located outside said housing;
said electrolyte comprising an ion-permeable microporous polymer gel formed in situ in said housing and filling said at least one hollow space;
said ion-permeable microporous gel comprising a polymer polymerized in situ in said housing in a suspension of silica gel in a saturated aqueous solution of a neutral salt containing suspended neutral salt particles;
said silica gel incorporated in said ion-permeable microporous polymer gel rendering the measuring probe pressure resistant to pressures in excess of 10 bars;
said predetermined electrode potential of said electrode being negligibly variable with pressure and pressure variations in the range of environmental pressure in excess of 10 bars due to the presence of said silica gel;
the neutral salt forming said saturated aqueous solution containing ions having predetermined transport numbers;
said neutral salt particles suspended in said saturated aqueous solution being substantially homogeneously distributed throughout said ion-permeable microporous polymer gel and containing ions having transport numbers which are substantially the same as said predetermined transport numbers of said neutral salt dissolved in said saturated aqueous solution;
said ion-permeable microporous polymer gel constituting an optically substantially clear polymer gel in the absence of said neutral salt particles but assuming a turbid appearance in the presence of said neutral salt particles substantially homogeneously distributed throughout said ion-permeable microporous polymer gel;
said electrolyte, during continued use of the measuring probe, aging due to continuous depletion of said neutral salt particles; and
said electrolyte possessing a distinct phase boundary formed between an optically substantially clear first zone which is depleted of said neutral salt particles, and a turbid second zone which still contains said neutral salt particles, and said distinct phase boundary assuming in said housing a lengthwise position which is dependent upon and indicative of the state of aging of said measuring probe.

* * * * *